United States Patent
Keyser et al.

(10) Patent No.: US 10,390,818 B2
(45) Date of Patent: Aug. 27, 2019

(54) FERRULE FOR USE WITH A MINIMALLY INVASIVE SURGICAL SUTURING DEVICE

(71) Applicant: LSI Solutions, Inc., Victor, NY (US)

(72) Inventors: Mark William Keyser, Bloomfield, NY (US); Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 57 days.

(21) Appl. No.: 15/241,613

(22) Filed: Aug. 19, 2016

(65) Prior Publication Data

US 2017/0049439 A1 Feb. 23, 2017

Related U.S. Application Data

(60) Provisional application No. 62/207,036, filed on Aug. 19, 2015.

(51) Int. Cl.
*A61B 17/04* (2006.01)
*A61B 17/06* (2006.01)

(52) U.S. Cl.
CPC ........... *A61B 17/0469* (2013.01); *A61B 2017/06014* (2013.01); *A61B 2017/06042* (2013.01)

(58) Field of Classification Search
CPC .......... A61B 17/06004; A61B 17/0469; A61B 2017/06009; A61B 17/06195; Y10T 16/39; Y10T 16/42; Y10T 29/49927; Y10T 29/49929; Y10T 29/49931; F16G 11/02
USPC ....... 606/139–148, 222–232; 385/60–68, 72, 385/78–85
See application file for complete search history.

(56) References Cited

U.S. PATENT DOCUMENTS

| | | | |
|---|---|---|---|
| 2,240,330 A * | 4/1941 | Flagg | A61B 17/06004 223/102 |
| 5,051,543 A * | 9/1991 | McGuire | H01R 4/203 16/108 |
| 5,431,666 A | 7/1995 | Sauer | |
| 5,562,686 A | 10/1996 | Sauer | |
| 5,766,183 A | 6/1998 | Sauer | |
| 6,368,334 B1 | 4/2002 | Sauer | |
| 6,533,796 B1 | 3/2003 | Sauer | |
| 6,997,931 B2 | 2/2006 | Sauer | |

(Continued)

OTHER PUBLICATIONS

Nov. 20, 2017 International Search Report from PCT Application PCTUS2017047593.

(Continued)

*Primary Examiner* — Kathleen S Holwerda
(74) *Attorney, Agent, or Firm* — David J. Gervasi; Christopher B. Miller

(57) ABSTRACT

A ferrule is disclosed for use with a surgical suturing device. The ferrule has a suture interface and a needle receptacle. The ferrule also has one or more indentations protruding into the needle receptacle. The ferrule further has one or more slits adjacent the one or more indentations. Another ferrule is disclosed for use with a surgical suturing device. The ferrule has a suture interface and a needle receptacle. The ferrule also has three indentations protruding into the needle receptacle. The ferrule further has three slits, each of the slits substantially centered between a different pair of indentations from the three indentations, and wherein each of the slits is longer and thinner than any one of the three indentations.

14 Claims, 2 Drawing Sheets

(56) References Cited

U.S. PATENT DOCUMENTS

| | | |
|---|---|---|
| 7,211,093 B2 | 5/2007 | Sauer |
| 7,407,505 B2 | 8/2008 | Sauer |
| 7,731,727 B2 | 6/2010 | Sauer |
| 8,313,496 B2 | 11/2012 | Sauer |
| 8,398,657 B2 | 3/2013 | Sauer |
| 8,517,073 B2 * | 8/2013 | Bogart ............... A61B 17/0487 156/499 |
| 8,652,149 B2 | 2/2014 | Sauer |
| 2002/0107530 A1 | 8/2002 | Sauer |
| 2004/0068272 A1 | 4/2004 | Sauer |
| 2005/0165419 A1 | 7/2005 | Sauer |
| 2007/0255296 A1 | 11/2007 | Sauer |
| 2009/0222027 A1 | 9/2009 | Sauer |
| 2010/0211083 A1 | 8/2010 | Sauer |
| 2011/0118758 A1 | 5/2011 | Sauer |
| 2012/0016383 A1 | 1/2012 | Sauer |

OTHER PUBLICATIONS

Sep. 21, 2016 Web Page; http://www.lsisolutions.com/rdquickloadsuture; , , LSI Solutions—RD Quick Load Suture.

* cited by examiner

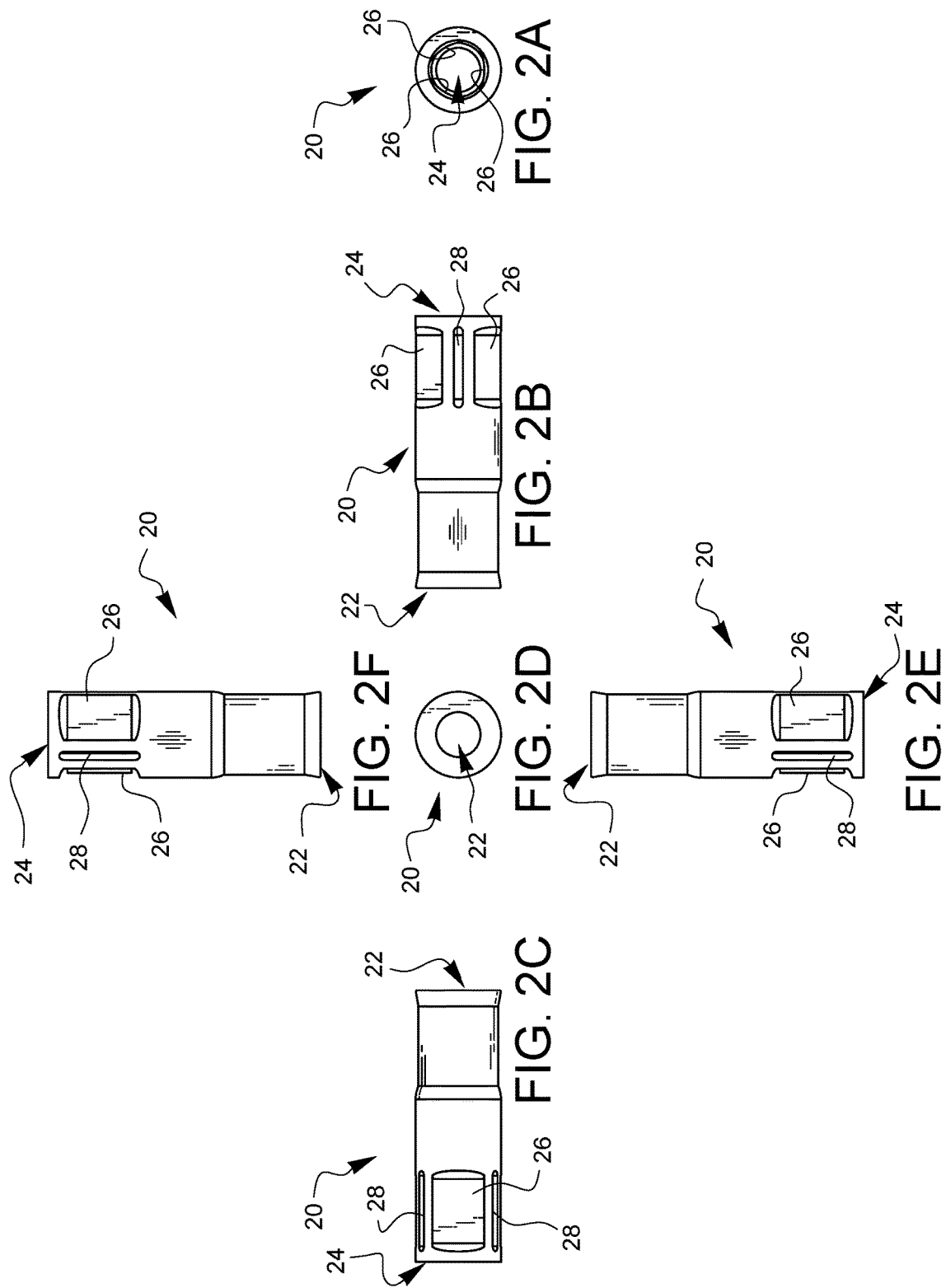

FERRULE FOR USE WITH A MINIMALLY INVASIVE SURGICAL SUTURING DEVICE

RELATED APPLICATION

This patent application claims priority to U.S. Provisional Patent Application No. 62/207,036 filed Aug. 19, 2015 and entitled "FERRULE FOR USE WITH A MINIMALLY INVASIVE SURGICAL SUTURING DEVICE". The 62/207,036 application is hereby incorporated by reference in its entirety.

FIELD

The claimed invention relates to surgical suturing devices, and more specifically to a ferrule for use with a minimally invasive surgical suturing device.

BACKGROUND

The recent advancement of minimally-invasive surgical procedures has proven to be an advantageous alternative over prior invasive surgical procedures. Advantages gained by minimally-invasive surgical procedures include quicker recovery time as well as a reduction in the length of hospital stays and medical costs.

Generally, minimally invasive surgery involves incising through body walls, for example, viewing and/or operating on the heart, ovaries, uterus, gall bladder, bowels, kidneys, appendix, etc. In one instance of such surgery, a trocar assembly is utilized for creating the incisions through which the endoscopic surgery is performed. The trocar assembly may include a sharp pointed obturator which is used to puncture and penetrate the skin and surrounding tissue to reach the surgical site. The obturator is positioned within a cannula which is generally configured as a sleeve member. The cannula remains in place after the obturator has been removed and provides a path for the insertion of surgical equipment needed for the particular surgical procedure.

Typically, a camera or endoscope is inserted through a cannula thereby enabling the visual inspection and magnification of the body cavity. With the visual assistance of an endoscope and external television monitor, the surgeon can perform diagnostic and therapeutic procedures at the surgical site with the aid of specialized instrumentation, such as, graspers, dissectors, electrocautery devices, and the like which are specifically designed for introduction and manipulation through additional cannulas.

Thus, instead of a large incision (typically 4-12 inches or larger) that cuts through major muscles, patients undergoing endoscopic surgery receive more cosmetically appealing incisions, which are typically between 5 and 10 millimeters in size, or smaller. Recovery is, therefore, much quicker.

In many minimally invasive surgical procedures, including those involved in endoscopic surgery, it is often necessary to suture organs or tissue and thereafter knot the suture material so as to approximate or adjoin tissue pieces. Such procedures may be especially challenging during minimally invasive surgery because of the small openings through which the suturing of the organs or tissues must be accomplished.

In the past, suturing of tissue through endoscopic surgery was achieved through the use of a sharp suture needle attached to an end of a length of suture material. In a typical endoscopic surgical procedure, the surgeon grasps the suture needle with an endoscopic grasping instrument, enabling the suture needle to be introduced into the abdominal body cavity of the patient, via a cannula. Through manipulation of the grasping instrument, the surgeon causes the suture needle to penetrate and pass through tissue, thereby also pulling the suture material therethrough. Unfortunately, using a grasping instrument with a suture needle is time consuming and burdensome due to the difficult maneuvers and manipulations which are required through the small endoscopic openings.

Fortunately, suturing devices for minimally invasive surgery have been developed which obviate the difficult suturing maneuvers which had been previously necessary. For example, U.S. Pat. No. 5,431,666 to Sauer et al; U.S. Pat. No. 5,766,183 to Sauer; U.S. Pat. No. 6,641,592 to Sauer; U.S. Pat. No. 7,211,093 to Sauer et al; U.S. Pat. No. 7,731,727 to Sauer; U.S. Pat. No. 8,398,657 to Sauer; and U.S. Pat. No. 8,926,640 to Sauer et al disclose a variety of useful surgical suturing devices for use with minimally invasive surgery, and those patents are all hereby incorporated by reference in their entirety. Similar devices are also commercially available from LSI Solutions, Inc., of Victor, N.Y., such as, but not limited to the RD180® suturing device. (See, for example, www.lsisolutions.com) Such suturing devices feature, among other things, a needle which may be actuated from a first position, through tissue positioned in a tissue bite area, and into contact with a ferrule at a second position. The ferrule is attached to a suture, and is taught to have an inner diameter which is slightly smaller than the outer diameter of the sharpened ends of the needle which contacts it. Thus, when the sharpened ends of the needle contact (are inserted into) the ferrule, friction holds the ferrule onto the sharpened end. The needle may then be moved back through the tissue to its starting position, pulling the ferrule and its attached suture along with it through the tissue. It is important to have a good fit (not too loose) between the needle tip and ferrule so that the ferrule remains engaged while being pulled through the tissue. It is also important in some embodiments that the ferrule not be attached too tightly to the needle, since some suturing devices can release the ferrule from the needle for the convenience of the operator, or even reset the ferrule (by removing it from the needle and putting it back in a starting position) for one or more additional stitches. In cases where the ferrule will be re-used, it is important that the frictional hold of the ferrule on the needle does not deform or stretch the ferrule to the point where it cannot reliably be used for multiple stitches. To address this, the dimensions of needle tips and inner diameters of ferrules in the prior art have exacting tolerances.

The popularity of these types of minimally invasive suturing devices has led to their growing use in a variety of different surgical procedures. As new suturing devices are developed, they may often benefit from needles of different sizes, shapes, and orientations. Correspondingly, different ferrules are often needed for mating with each new or different type of needle in a surgical suturing device. Not only does this lead to the need for customers to purchase and track different kinds of ferruled sutures for different procedures, it can make it difficult for surgeons to utilize a single suture with multiple suturing devices.

Therefore, there is a need for an improved ferrule which can reliably function with a variety of existing suturing devices for a range of different needle types and dimensions.

SUMMARY

A ferrule is disclosed for use with a surgical suturing device. The ferrule has a suture interface and a needle receptacle. The ferrule also has one or more indentations protruding into the needle receptacle. The ferrule further has one or more slits adjacent the one or more indentations.

Another ferrule is disclosed for use with a surgical suturing device. The ferrule has a suture interface and a needle receptacle. The ferrule also has three indentations protruding into the needle receptacle. The ferrule further has three slits, each of the slits substantially centered between a different pair of indentations from the three indentations, and wherein each of the slits is longer and thinner than any one of the three indentations.

BRIEF DESCRIPTION OF THE DRAWINGS

FIGS. 2A, 2B, 2C, 2D, 2E, and 2F are front, left, right, back, top, and bottom views, respectively, of the ferrule embodiment from FIG. 1.

Figure 1:
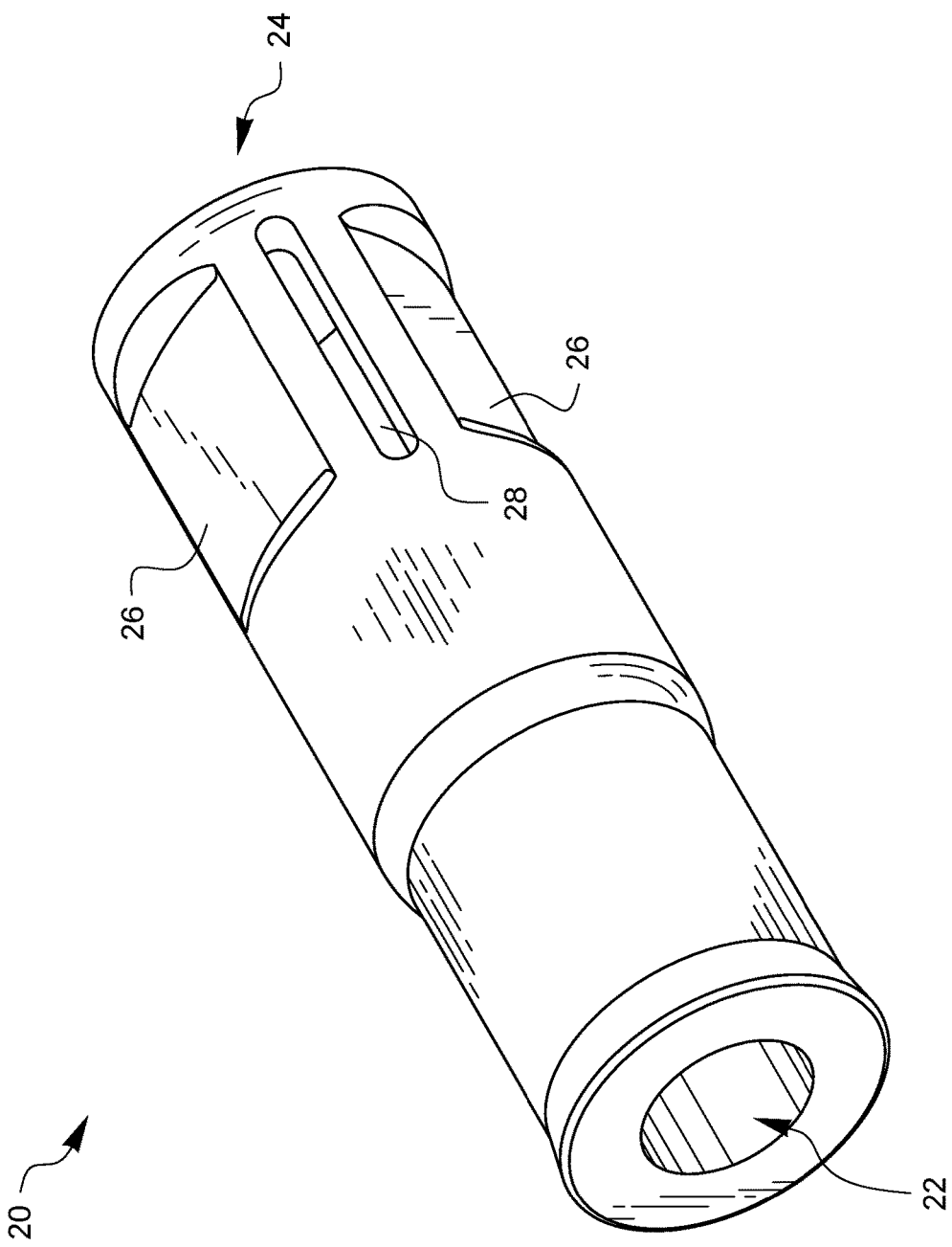
FIG. 1 is a perspective view of one embodiment of an improved ferrule for use with a surgical suturing device.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1 is a perspective view of a ferrule 20 for use with a surgical suturing device. FIGS. 2A, 2B, 2C, 2D, 2E, and 2F are front, left, right, back, top, and bottom views, respectively, of the ferrule embodiment from FIG. 1. The ferrule 20 has a suture interface 22 which is configured to be coupled to a suture. It should be understood that the term "suture", as used herein, is intended to cover any thread, cable, wire, filament, strand, line, yarn, gut, or similar structure, whether natural and/or synthetic, in monofilament, composite filament, or multifilament form (whether braided, woven, twisted, or otherwise held together), as well as equivalents, substitutions, combinations, and pluralities thereof for such materials and structures. Although a suture is not illustrated as being coupled to the suture interface 22, those skilled in the art are familiar with a variety of techniques to reliably couple the suture to the suture interface 22, including, but not limited to crimping, gluing, welding, melting, heating, and pressing.

The ferrule 20 also has a needle receptacle 24. In this embodiment, the needle receptacle 24 is on an opposite end from the suture interface 22. The needle receptacle 24 has a substantially round opening which extends into the body of the ferrule 20. The ferrule 20 also has multiple indentations 26 which protrude into the needle receptacle 24. Other embodiments may have fewer or more indentations in the needle receptacle 24. The indentations 26 are positioned to contact a needle tip which may be moved into the needle receptacle 24 of the ferrule 20. Interference/friction between the needle tip (not shown) and the indentations 26 enables the ferrule 20 to remain coupled to the needle tip.

The ferrule 20 also has multiple slits 28 adjacent the one or more indentations 26. Other embodiments may have fewer or more slits. In this embodiment, the ferrule 20 has three indentations 26 which are of similar size, spaced substantially equally around the needle receptacle 24. Similarly, in this embodiment, the ferrule 20 has three slits 28 which are of similar size, spaced substantially equally around the needle receptacle 24. In this embodiment, the slits 28 are thinner and longer than the indentations 26, and the slits 28 are approximately centered between the indentations 26 to which they are adjacent. One suitable non-limiting width (the shorter dimension) of the slit 28 may be approximately 0.001 inch. Other embodiments may have different dimensions and/or spacings of the indentations and the slits.

The slits 28 allow each of the indentations 26 to flex independently, thereby enabling the ferrule 20 to accommodate a variety of different needle diameters and shapes without permanently deforming. This has not been possible with previous ferrule designs, and the resultant ability for a single ferrule to work with a range of needle sizes and shapes enables simplification of surgical equipment ordering, allows surgeons to use a single suture with multiple minimally invasive surgical suturing devices without the need for those devices to have the same needle configuration, and ensures reliable re-use of the ferrule in multiple stitch situations where the needle and ferrule will come together and separate repeatedly.

Various advantages of a ferrule for use with a minimally invasive surgical suturing device have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Embodiments of ferrules may be made from a variety of materials, including, but not limited to metals, alloys, and plastics. Accordingly, the invention is limited only by the following claims and equivalents thereto.

What is claimed is:

1. A ferrule for use with a surgical suturing device, comprising:
    a suture interface;
    a needle tip receptacle;
    three indentations protruding into the needle tip receptacle; and
    three slits, each of the slits substantially centered between a different pair of indentations from the three indentations, wherein the slits do not contact the three indentations, and wherein each of the slits is longer and thinner than any one of the three indentations.

2. The ferrule of claim 1, wherein each of the three indentations flex independently from one another.

3. The ferrule of claim 1, further comprising a substantially cylindrical body that defines the suture interface, the needle tip receptacle, and the three slits, and in which the three indentations are formed.

4. The ferrule of claim 1, wherein the suture interface comprises a substantially round opening.

5. The ferrule of claim 1, wherein the needle tip receptacle comprises a substantially round opening.

6. The ferrule of claim 1, wherein the three indentations all have the same dimensions.

7. The ferrule of claim 1, wherein the three slits all have the same dimensions.

8. The ferrule of claim 1, wherein the three indentations are spaced substantially equally around the needle tip receptacle.

9. The ferrule of claim 1, wherein the three slits are spaced substantially equally around the needle tip receptacle.

10. The ferrule of claim 1, wherein the three slits are longer and thinner than the three indentations.

11. The ferrule of claim 1, wherein the three slits are approximately 0.001 inches wide.

12. The ferrule of claim 1, wherein the suture interface is smaller than the needle tip receptacle.

13. The ferrule of claim 1, wherein the suture interface has a smaller diameter than the needle tip receptacle.

14. The ferrule of claim 1, further comprising a suture coupled to the suture interface.

\* \* \* \* \*